US011638621B2

(12) United States Patent
Vanliefde et al.

(10) Patent No.: US 11,638,621 B2
(45) Date of Patent: May 2, 2023

(54) BASKET FOR A MEDICAL INSTRUMENT BASKET AND MEDICAL INSTRUMENTS

(71) Applicant: BELINTRA NV, Semmerzake (BE)

(72) Inventors: Charlotte Vanliefde, Semmerzake (BE); Peter Van Der Vennet, Semmerzake (BE)

(73) Assignee: BELINTRA NV, Semmerzake (BE)

( * ) Notice: Subject to any disclaimer, the term of this patent is extended or adjusted under 35 U.S.C. 154(b) by 1112 days.

(21) Appl. No.: 16/316,094

(22) PCT Filed: Jul. 7, 2017

(86) PCT No.: PCT/EP2017/067056
§ 371 (c)(1),
(2) Date: Jan. 8, 2019

(87) PCT Pub. No.: WO2018/011070
PCT Pub. Date: Jan. 18, 2018

(65) Prior Publication Data
US 2021/0275271 A1    Sep. 9, 2021

(30) Foreign Application Priority Data
Jul. 11, 2016  (BE) .................................. 2016/5581

(51) Int. Cl.
*A61B 50/34*    (2016.01)
*A61L 2/07*    (2006.01)
(Continued)

(52) U.S. Cl.
CPC ................ *A61B 50/34* (2016.02); *A61L 2/07* (2013.01); *A61L 2/26* (2013.01); *B65B 55/027* (2013.01);
(Continued)

(58) Field of Classification Search
CPC ............ A61B 50/34; A61B 2050/3006; A61L 2202/23
(Continued)

(56) References Cited

U.S. PATENT DOCUMENTS 2,968,418 A * 1/1961 Stoddard ............ B65D 21/0211
206/509
3,338,466 A * 8/1967 Hare .................... B65D 21/046
211/126.9
(Continued)

FOREIGN PATENT DOCUMENTS

DE      100 46 757 C1    2/2002
DE      100 42 083 A1    3/2002
NL      1 004 306 C1     4/1998

OTHER PUBLICATIONS

PCT International Search Report and Written Opinion dated Oct. 9, 2017 for PCT International Patent Application No. PCT/EP2017/067056, 9 pages.

*Primary Examiner* — Robert F Long
*Assistant Examiner* — Xavier A Madison
(74) *Attorney, Agent, or Firm* — Amster, Rothstein & Ebenstein LLP (57) ABSTRACT

Described herein is a holding basket (100) for containing an inner basket (200) for holding at least one medical item for processing having a top end (102) and a base end (104) comprising: an essentially rectangular base (110) and side walls (120, 122, 124) extending from the base (110), two rims (130, 132) each disposed on a first pair (120, 122) of opposing side walls, two windows 140) each disposed on a second pair opposing side walls (124) configured for manual access for slidable removal of the inner basket (200), wherein the holding basket (100) is configured for stackability or nestability with an adjacent holding basket (100', 100").

9 Claims, 4 Drawing Sheets (51) Int. Cl.
*A61L 2/26* (2006.01)
*B65B 55/02* (2006.01)
*A61B 50/30* (2016.01)

(52) U.S. Cl.
CPC ............ *A61B 2050/3006* (2016.02); *A61B 2050/3007* (2016.02); *A61L 2202/23* (2013.01); *A61L 2202/24* (2013.01)

(58) Field of Classification Search
USPC ........................................... 53/425
See application file for complete search history.

(56) References Cited

U.S. PATENT DOCUMENTS

| | | | | |
|---|---|---|---|---|
| 3,366,264 | A * | 1/1968 | Panknin | B65D 21/046 |
| | | | | 206/505 |
| 6,840,593 | B2 * | 1/2005 | Remmers | A47B 88/427 |
| | | | | 312/334.44 |
| 6,969,133 | B2 * | 11/2005 | Compagnucci | A47B 88/427 |
| | | | | 312/334.6 |
| 7,438,185 | B2 * | 10/2008 | Ho | B65D 21/0212 |
| | | | | 206/509 |
| 9,205,158 | B1 * | 12/2015 | Jacob | A61L 2/04 |
| 9,351,570 | B2 * | 5/2016 | Koefelda | A47B 55/00 |
| D793,087 | S * | 8/2017 | Goodman | D3/306 |
| 9,968,695 | B2 * | 5/2018 | Duddy | A61L 2/26 |
| 10,111,972 | B2 * | 10/2018 | Mauzerall | A47B 91/16 |
| 2005/0249651 | A1 * | 11/2005 | Riley | A61B 50/22 |
| | | | | 206/363 |
| 2010/0000900 | A1 | 1/2010 | Hassell | |
| 2012/0152289 | A1 | 6/2012 | Smith et al. | |
| 2015/0151875 | A1 | 6/2015 | Hassell et al. | |

\* cited by examiner

BASKET FOR A MEDICAL INSTRUMENT BASKET AND MEDICAL INSTRUMENTS

CROSS-REFERENCE TO RELATED APPLICATIONS

This application is a U.S. national stage entry under 35 U.S.C. § 371 of PCT International Patent Application No. PCT/EP2017/067056, filed Jul. 7, 2017, which claims priority to Belgian Patent Application No. 2016/5581, filed Jul. 11, 2016, the contents of which are incorporated herein by reference in their entirety.

FIELD OF THE INVENTION

Provided herein is a holding basket for holding at least one medical item, preferably disposed in a removable inner basket for processing which holding basket is configured for stackability and nestability with an adjacent holding basket.

BACKGROUND

In medical practices baskets may be used for transport, storage and processing of various items, including boxes, cases or medical items, such as surgical instruments or glassware. Commonly, their use in a medical procedure then necessitates a thorough cleaning and/or sterilization procedure. This safe processing is necessary to fulfil the strict clinical protocols set by the medical industry. To reduce the chance for structural damage or user mishandling, the baskets are often stored in a storage system, such a shelf or a rack, which may by itself be part of a transport system, such as a hospital tray delivery cart. However, the existing baskets suffer from numerous deficiencies related to a lack in convenience of use, storable and stackable space, and/or related to the safety of storage and withdrawal of the basket's inner contents after processing.

For instance, when a box or container e.g. an inner basket is placed inside a basket its sidewalls may abut the inner surface of the basket, which can make withdrawal of said box or container cumbersome. This issue is especially common when such a box is wrapped in a non-woven textile, which may be necessary for certain cleaning and/or sterilization procedure. Also, baskets tend to have a suboptimal design, with little to no regard for optimizing storage or packing space. When spread out over numerous baskets, such as tens or hundreds of baskets, hospital may lose precious space which could otherwise be utilized more efficiently.

DE 100 46 757 and NL 1004306 describe a basket for sterilizing items having four continuous side walls. Extraction of an inner basket that tightly occupies the holding space requires inversion or a high degree of manual dexterity. Due to the presence of lower hooks or protrusions and lack of suitable rims the baskets are not suited for placement in a typical storage/transport slide rack system. US 2010/0000900 describes a bakery basket that is not suitable for medical applications being made from molded plastic, and not being suited for placement in a typical storage/transport slide rack system.

Accordingly there is a need for solutions which allow for the improved safe storage, processing and removal of medical items. Accordingly there is a need for a basket, known here as a holding basket, for holding at least one medical item which overcomes the problems of the art.

SUMMARY

Described herein is a holding basket (100) for containing an inner basket (200) for holding at least one medical item for processing having a top end (102) and a base end (104) comprising:
  an essentially rectangular base (110) and side walls (120, 122, 124) extending from the base (110),
  two rims (130, 132) each disposed on a first pair (120, 122) of opposing side walls,
  two windows (140) each disposed on a second pair opposing side walls (124) configured for manual access for slidable removal of the inner basket (200),
  wherein the holding basket (100) is configured for stackability or nestability with an adjacent holding basket (100', 100").

Further described herein is a holding basket (100) for containing an inner basket (200) for holding at least one medical item for processing having a top end (102) and a base end (104) comprising:
  an essentially rectangular base (110) and side walls (120, 122, 124) extending from the base (110),
  only two rims (130, 132) configured for sliding into a slide rack each such rim disposed on a first pair (120, 122) of opposing side walls,
  two windows (140) each disposed on a second pair opposing side walls (124) configured for manual access for slidable removal of the inner basket (200),
  wherein the holding basket (100) is configured for stackability or nestability with an adjacent holding basket (100', 100").

The holding basket (100) may be configured for stackability or nestability with an adjacent holding basket (100', 100") when the rims (130, 132) on the respective holding baskets (100, 100', 100") are aligned in a vertical direction, being stackable or nestible dependent on the relative orientation of the adjacent holding baskets (100, 100', 100").

The base (110) and/or the side walls (120, 122, 124) may be formed essentially from wire.

Each rim (130, 132) may be disposed essentially parallel to the base (110).

Each window (140) may have an edge opening at a top end (102).

The holding basket (100) may have only two rims (130, 132).

Each of the side walls (120, 122, 124) may be at least partly tapered, narrowing towards the base end (104).

The holding basket (100) may be configured such that:
  each of two opposing edges of the top end (102) of the holding basket (100) is provided with an arrangement of tabs (T) and gaps (G) and the edge at the base end (104) of the holding basket (100) is provided with an inverse arrangement of tabs and gaps compared with the corresponding top edge,
  an arrangement of tabs and gaps at one of the opposing edges is an inverse of the arrangement of tabs and gaps at other of the opposing edges, said tabs and gaps arranged such that:
  the tabs at the base end (104) of an adjacent holding basket (100') align and contact the tabs at the top end of the holding basket (100) such that the adjacent holding basket (100') can stack over the holding basket (100) when the holding basket (100) and the adjacent holding basket (100') adopt a first mutual orientation, and
  the tabs at the base end (104) of an adjacent holding basket (100') slide into the gaps of the holding basket (100), and the tabs at the top end (102) of the holding basket (100) slide into the gaps at the base end (104) of the adjacent holding basket (100') such that the adjacent holding basket (100') can nest into the holding basket (100) when the adjacent holding basket (100') is rotated 180 deg about an axis perpendicular to the base (110) relative with the holding basket (100) starting from the first mutual orientation.

The adjacent basket (100') may be a copy of a holding basket (100) as described above.

Further described herein is a method for sterilising one or more medical equipment items comprising:
placing the one or more medical equipment items into an inner basket (200),
placing the inner basket (200) into a holding basket (100) as described herein,
stacking holding basket (100) relative to an adjacent holding basket (100'),
sliding the holding basket (100) into a storage system that is a slide rack,
placing the storage system into an autoclave and autoclaving, and
removing the storage system from the autoclave.

Further described herein is a use of the holding basket (100) as described herein for processing medical equipment, wherein the processing includes a step of autoclaving.

BRIEF DESCRIPTION OF THE DRAWINGS

The numeric references may be found discussed in detail in the Figures section below.

FIG. 8 shows in Panel A a plan view of an arrangement of gaps and tabs at the top end of a holding basket, in Panel B a plan view of an arrangement of gaps and tabs at the base end of a holding basket, in Panel C a holding basket and an adjacent holding basket oriented for stacking, in Panel D a holding basket and an adjacent holding basket oriented for nesting, Throughout the figures, the following numbering is adhered to:

100—holding basket; 100'—adjacent holding basket; 100"—adjacent holding basket; 102—top end; 104—base end; 110—essentially rectangular base; 130—first rim; 132—second rim; 120 and 122—first pair opposing side walls; 124—one wall of second pair opposing side walls; 106 and 106'—imaginary orientation markers; 140—window; 150—nesting stop member; 160—holding space; 200—inner basket.

DETAILED DESCRIPTION

Before the present device i.e. holding basket and method of the invention are described, it is to be understood that this invention is not limited to particular systems and methods or combinations described, since such systems and methods and combinations may, of course, vary. It is also to be understood that the terminology used herein is not intended to be limiting, since the scope of the present invention will be limited only by the appended claims. As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. It will be appreciated that the terms "comprising", "comprises" and "comprised of" as used herein comprise the terms "consisting of", "consists" and "consists of".

The recitation of numerical ranges by endpoints includes all numbers and fractions subsumed within the respective ranges, as well as the recited endpoints.

The term "about" or "approximately" where used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" or "approximately" refers is itself also specifically, and preferably, disclosed.

Whereas the terms "one or more" or "at least one", such as one or more or at least one member(s) of a group of members, is clear per se, by means of further exemplification, the term encompasses inter alia a reference to any one of said members, or to any two or more of said members, such as, e.g., any ≥3, ≥4, ≥5, ≥6 or ≥7 etc. of said members, and up to all said members.

All references cited in the present specification are hereby incorporated by reference in their entirety. In particular, the teachings of all references herein specifically referred to are incorporated by reference.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the claimed embodiments can be used in any combination.

In the present description of the invention, reference is made to the accompanying drawings that form a part hereof, and in which are shown by way of illustration only of specific embodiments in which the invention may be practiced. Parenthesized or emboldened reference numerals affixed to respective elements merely exemplify the elements by way of example, with which it is not intended to limit the respective elements. It is to be understood that other embodiments may be utilised and structural or logical changes may be made without departing from the scope of the present invention. The following detailed description, therefore, is not to be taken in a limiting sense, and the scope of the present invention is defined by the appended claims.

Figure 1:
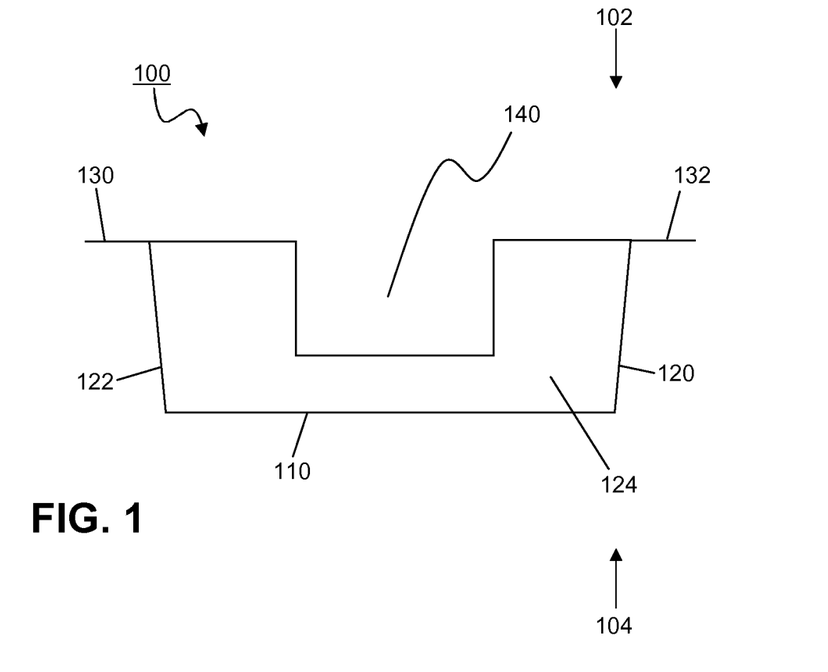
FIG. 1 shows a schematic of a holding basket (100).

Provided herein is a holding basket. It may be used, for example, holding an inner basket, such as a box or a case, or for holding at least one medical item, such as surgical instruments or glassware. The medical item is typically autoclavable. Examples of surgical instruments include cutting, grasping or holding instruments, haemostatic forceps (i.e., instruments used to stop blood flow), retractors, clamps, distractors, accessories, syringes, and the like. Additionally or alternatively, clothing may be held within the holding basket. An exemplary holding basket is shown in FIG. 1, and is described more in detail elsewhere herein. The holding basket thus foresees a solution to one or more of the problems described above.

According to one aspect the holding basket fulfills the role of a container which is used for containing an inner basket, and/or partially or fully encloses a held medical item as described herein. The holding basket comprises side windows which according to an embodiment of the invention improve the holding basket's convenience of use, by allowing an inner basket and/or medical item to be more conveniently placed into and subsequently withdrawn from the holding basket. Further, the holding basket is disposed with two rims which may serve dual purposes, namely they may allow the basket to be slid into a storage system, such as slide rack or shelf, but they can also provide additional support during stacking. By limiting the rims to two opposite ends the basket the design leads to an increase in the basket holding space for the same footprint compared with a holding basket having circumferential rim i.e. around all four sides. It has particular effect when the holding basket is placed in a storage system of standard size e.g. in a sliding rack system; the basket holding space can be increased without change to the design of the storage system. Additionally, the holding basket as described herein is stackable in one direction and nestable in another direction, thus making a single basket multi-purpose, e.g. by providing a stackable basket for holding and a nestable basket for storage. The term rim herein refers to an outward protrusion from an upper edge of a side wall that engages with a sliding rack system.

The term "holding basket" as used herein refers to a container having a holding space bound by multi-aperture walls and having an open top. Most typically, the holding basket is formed essentially from a strand or strands of material that cross and which may be joined at one or more intersections. Typically the holding basket is a wire basket. The wire may be a metal such as steel or a polymer.

The term "inner basket" refers to a container having multi-apertures wall configured to fit inside the holding basket. It is preferred that the inner basket fittingly engages within the holding space of the holding basket. Most typically, the inner basket is formed essentially from a strand or strands of material that cross and which may be joined at one or more intersections. Typically the inner basket is a wire basket. The wire may be a metal such as steel or a polymer. The inner basket is typically rigid. The inner basket is used to hold sterilisable (e.g. autoclavable) medical equipment such as surgical devices.

The term "storage system" as used herein refers to any system typically comprising a framework configured for holding or storing of items. More specifically, for the purposes of the invention the storage system refers to a framework designed for holding at least one and preferably a plurality of holding baskets according to an embodiment of the invention. The storage system may be static, but may also be transportable in which case it will further comprise a transport means such as wheel. Examples of static storage systems are racks, shelves, frames, closets, and the like. Examples of transportable storage systems are carts, such as hospital delivery carts.

In some embodiments the holding basket comprises an essentially rectangular base and side walls extending from the base, two rims each disposed on a first pair of opposing side walls. The rims are preferably configured for engaging with opposing channels of a storage system that is a slide rack. The two rims are preferably each disposed on a top end of the first pair of opposing side walls. Two windows each disposed on a second pair opposing side walls configured for manual access for slidable removal of the inner basket, wherein the holding basket is configured for stackability and nestability. The second pair of side walls is typically different from the first pair or side walls. A top end of the holding basket opposite the base is open; the inner basket is introduced into the holding space of the holding basket through the open top. The holding basket may contain only two rims. The holding basket may contain only two windows. A holding space bound by multi-aperture walls and having an open top. The holding basket is rigid. The holding basket may be dimensioned for fitting engagement with a standardised hospital storage system such as a slide rack.

The holding basket gives rise to several advantages.

Firstly, the holding basket's base comprises an essentially rectangular shape, which is an optimal shape for the storage and stacking of multiple items. In some preferred embodiments the holding basket comprises an essentially rectangular base with rounded corners. These rounded corners may improve the stacking and removal of the inner basket contained in the holding basket. Moreover, rounded corners generally provide an improvement in the holding basket's safety and ease of use, for they prevent or at least diminish damages occurred to a held instrument and/or injury to a user of said holding basket in case of an accident, for example when the basket is dropped. Additionally, if the inner basket is wrapped for processing with a wrapping fabric, for example a blanket, towel or cloth, the rounded edges of the holding basket can also prevent any tearing of the wrapping fabric. Alternatively, a fully rectangular base having sharp corners may be used for the present invention.

Secondly, holding basket comprises two rims which can serve a dual purpose; namely, to allow the holding basket to be slid into a storage system such as a slide rack, but also to provide additional support and stability during stacking. With regards to the former, by limiting the rims to a first pair of opposing side walls the holding space can be increased for the same footprint, since the second pair of side walls effectively define an edge of a holding basket footprint and rather than rims. When the holding basket is stored in a standard sized storage systems such as a slide rack, addition holding space is gained at the front and the back of the holding basket, for instance. In some preferred embodiments the protrusion length of each rims, measured by the distance from the holding basket's side wall where the rim is connected to up to said rim's edge, preferably running parallel to said holding basket's outer wall, is dimensioned according to the slide rack's slidable engagement mechanism; for example, a set of rollers or shelves.

In some embodiments each rim is disposed essentially parallel to the base. This allows the rims to better serve as a base support for stacking holding baskets on top of one another, as a parallel, preferably flat, surface further stabilizes a stacked adjacent basket.

In some embodiments the protrusion length of each rim extends at most 50% over the slidable engagement mechanism of the slide rack; preferably at most 30%; more preferably at most 20%; most preferably at most 10%. By minimising the length of the rim protrusion, more of the footprint of the basket can be dedicated to holding space.

In some preferred embodiments the rims are connected to additional support structures, such as stabilising basket wires or strips. This allows the rims to support a heavy weight without losing structure or shape when, for instance several baskets are stacked, each basket containing at least one medical item or inner basket. This is particularly advantageous when carrying multiple baskets to a storage system.

In some embodiments, the rims contact a plane, preferably wherein the two rims are located in essentially the same plane. The plane is preferably essentially parallel to the base. The corners of the rims may form an essentially rectangular shape; preferably a rectangular shape with rounded corners. Similarly to the base, the rounded corners of the rims improve the basket's safety and ease of use. Preferably the essentially rectangular top runs parallel to the essentially rectangular bottom. This configuration is advantageous for a stacking of holding basket as the weight of an upper basket can be better spread out of the rim's edges, thereby spreading the full pressure.

Thirdly, the holding basket comprises two windows which improve the holding basket's convenience of use. Certain inner baskets may be provided in a certain volumetric shape, which is essentially the same or slightly smaller than the volumetric shape of the holding space. When said inner baskets are inserted into the holding basket holding space, their edges or walls will abut the walls of the basket, thus making their withdrawal difficult and cumbersome due to frictional effects. Additionally, if the inner basket is also wrapped in a non-woven textile, the withdrawal is hindered without the aid of tools due to the textile being compressed when it is pressed down in the base of the basket. The windows allow at least manual access to the inner basket for it to be withdrawn. This allows the volumetric shape of inner basket to be maximised. Moreover, during processing certain materials are prone to expand under the influence of the increased temperature, humidity or pressure of the processing procedure, such as autoclaving; the windows allow the application of a removal force to the inner basket for slidable removal of thereof. The windows also allow medical items of any materials to be stacked while reducing the risk of being lodged inside the basket during processing.

In some embodiments the holding basket has a top end and a base end, wherein the each window has an edge opening at a top end. The edge opening allows the application of a force to slide the inner basket upwards and clear of the holding basket in a continuous motion. This edge opening thus further improves the basket's convenience of use.

In some embodiments each window forms an essentially trapezoid shape, narrower at the base end and a broader at the top end; preferably the trapezoid shape has rounded corners.

Similar to the rounded base and rims, the rounded corners of the windows improve the holding basket's safety and ease of use.

In some embodiments, the essentially rectangular base and side walls are permanently attached. In case of an accident it is important the holding basket does not break which would cause a held medical item to spill or fall out of the holding basket. Preferably the holding basket also absorbs at least partially the external shock or pressure, thereby protecting the medical item at least partially from the full impact of the force of the accident. More preferably, in case of an accident involving stacked holding baskets, the rims form a stopping and absorbing element, preferably at least partially supporting the upper holding basket(s).

Fourthly, the holding basket as described herein is stackable in one direction and nestable in another direction, thus giving two functions to the same the holding basket e.g. by providing a stackable holding basket for holding and a nestable holding basket for storage. To achieve said configurations, the rims of the holding basket and at least one adjacent holding basket are aligned in a vertical direction. Whether the holding basket and adjacent holding basket are stacked or nested depends on the relative orientation of the adjacent holding baskets, as seen about a vertical axis, said axis preferably running perpendicular to the holding basket base. A change in mutual orientation of 180 deg effects the stacking or nesting mode between adjacent baskets.

In general, two holding baskets, a first holding basket and an adjacent holding basket each according to an embodiment of the invention, can engage in essentially two configurations; namely, a first nestable configuration wherein the adjacent holding basket is at least partially contained within the holding space of the first holding basket, and a second stackable configuration wherein the adjacent holding basket is not contained within the holding space of the first holding basket, but instead resting on top of the first holding basket. The choice of configuration results in a change of the holding space.

Figure 4:
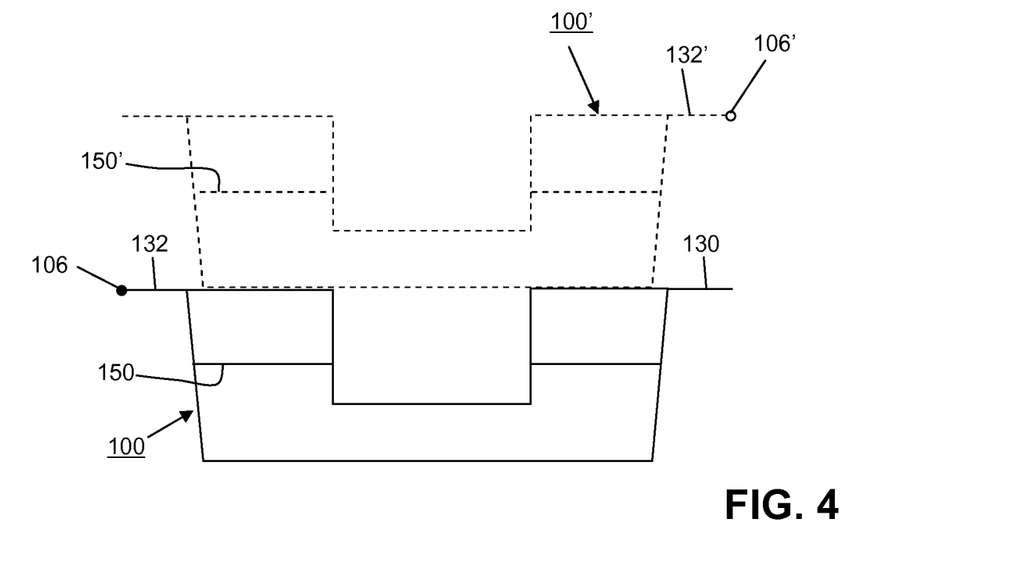
FIG. 4 illustrates how a first holding basket (100) and a second adjacent holding basket (100') can be stacked according to an embodiment of the present invention.

The stacking configuration is typically employed when there is a plurality of holding baskets, each containing an inner basket having a maximum volumetric shape complimentary to the volumetric shape of the holding space; multiple holding baskets can be stacked for storage or for processing while still containing a maximum sized inner basket. The stackable configuration is particularly beneficial for holding relatively large inner baskets, or for holding large gloveboxes, etc., or larger medical items, such as grasping or holding instruments, retractors, clothing, and the like. Preferably in the stackable configuration sufficient holding volume is provided to hold the inner basket and/or medical item without it coming in contact with the adjacent holding basket, thereby avoiding of at least reducing external pressure on said medical item. An example of the stackable configuration is illustrated in FIG. 4.

The nestable configuration is typically employed for storage when multiple holding baskets are not in use; the overall volume occupied by a plurality of nested holding baskets is significantly smaller compared with stacking so they can be efficiently stored. The nestable configuration may alternatively or in addition be employed when there is a plurality of holding baskets each containing an inner basket having a volumetric shape complimentary to the volumetric shape of the holding space but of a lower height; multiple holding baskets each containing an inner basket can be nested for storage or for processing.

Figure 3:
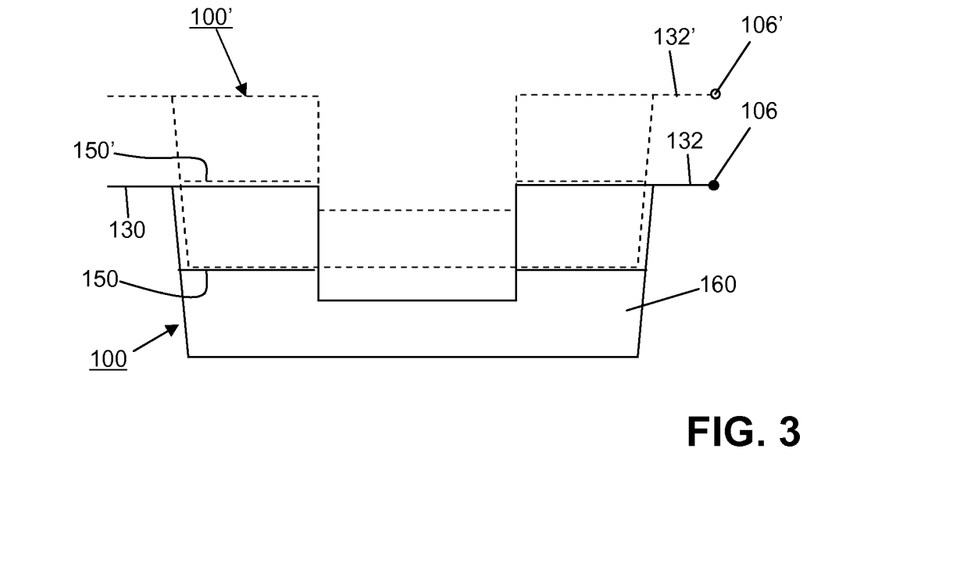
FIG. 3 illustrates how a first holding basket (100) and a second adjacent holding basket (100') can be slidably nested according to an embodiment of the present invention.

The nestable configuration is particularly beneficial for holding relatively small (reduced height) inner baskets, or small items such as pill or syringe cases, etc., or smaller medical items, such as cutting instruments, syringes, and the like. Especially for fragile medical items it may be pertinent to avoid stacking several medical items on top of each other in a holding basket. However, this would leave a holding basket at least partially empty when an adjacent holding basket is stacked, thereby wasting space and holding volume. To avoid said waste the adjacent holding basket may be contained at least partially, preferably contained about halfway, in the holding basket. An example of the nestable configuration is illustrated in FIG. 3.

In some embodiments the walls of the holding basket and the walls of the inner basket are configured for slidable engagement with each other. By configuring a sliding motion, the ease of use and safety of stacked baskets is improved. The lack of locking or latching mechanism may improve the stacking and removal speed. This is particularly advantageous for quickly stacking a plurality of holding baskets, which may be required of the users (i.e. hospital staff) processing a vast amount of baskets in a working day. Additionally or alternatively, once a basket is filled to the window by at least one inner basket and/or medical item, an adjacent basket can be slid on top for quickly nesting a plurality of holding baskets, thereby also improving the filling speed when using a plurality of nesting holding baskets. Similar advantages are present when working in the other direction, for instance when dividing stacked and/or nested holding baskets the lack of a mechanism allows a faster division of holding baskets.

In some embodiments the holding basket and adjacent holding basket are alike according to an embodiment of the invention. The holding baskets may comprise different embodiments of the invention, for example, the holding basket may have differently shaped windows from the adjacent holding basket; However, alike as used herein refers to the dimensions of the holding basket and adjacent holding basket differing less than 20% in terms of height, width and depth. In some preferred embodiments the holding basket and adjacent holding basket are similar according to an embodiment of the invention. Similar as used herein refers to the dimensions of the holding basket and adjacent holding basket differing less than 10% in terms of height, width and depth. In some most preferred embodiments the holding basket and adjacent holding basket are identical according to an embodiment of the invention. Identical as used herein refers to the dimensions of the holding basket and adjacent holding basket differing less than 5% in terms of height, width and depth, according to potential production errors.

In some embodiments each of the side walls is at least partly tapered, narrowing towards the base. Tapered side walls improve the nestability of the basket, by allowing the nested adjacent holding basket to be inserted more smoothly along the side walls; this way any fall damage is minimized if the adjacent holding basket would be dropped into the basket. This way also the security is improved for any inner baskets and/or medical items which might be contained within the basket when an adjacent basket is nested.

Figure 8:
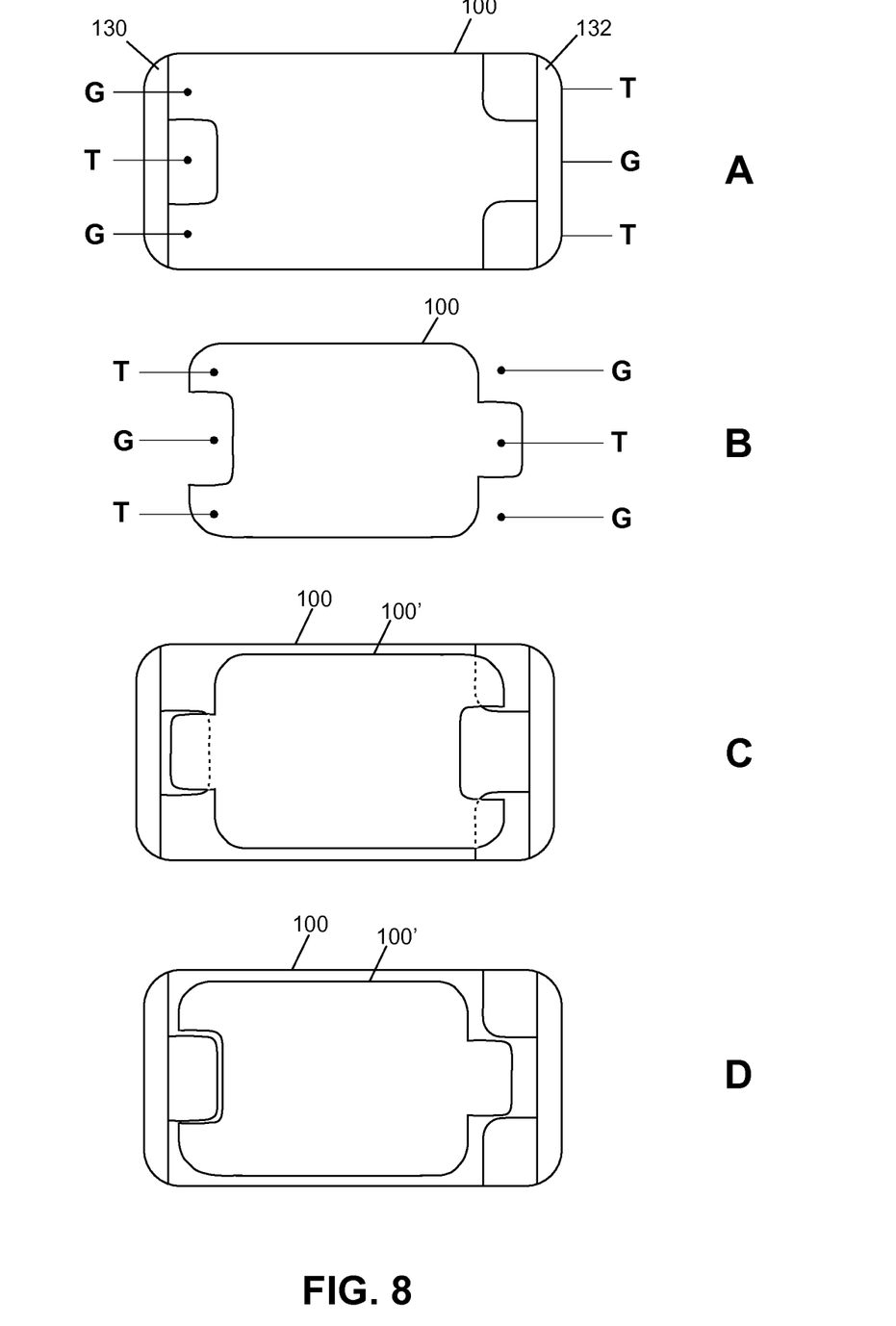

The directional nesting and stacking capability of the holding basket can be achieved by any known means in the art. According to one aspect, each of two opposing edges of the top end of the holding basket is provided with an arrangement of tabs and gaps and each edge at the base end of the holding basket is provided with an inverse arrangement of tabs and gaps compared with the corresponding top edge. By inverse, it is meant that where a top edge is provided with a gap, it is replaced by a tab in the corresponding position at the base edge. The arrangement of tabs and gaps at one of the opposing edges is an inverse of the arrangement of tabs and gaps at other of the opposing edges. By inverse, it is meant that where a slot is provided along one top edge with a gap, it is replaced by a tab in the corresponding position along the opposing top edge. An exemplary arrangement is shown in FIGS. 8A and B. The inverse arrangement of gaps and tabs allows the tabs of a first holding basket to slide into the gaps of second holding basket when the holding baskets are oriented for nesting, and allows the tabs of a first holding basket to rest on the second holding basket when the holding baskets oriented for stacking. The tabs and gaps may be realized when the holding basket is made substantially from wire by suitably shaping wire strands. The number of tabs and gaps per edge is preferably 3.

In some embodiments the first pair of side walls each contains is at least partly tapered, narrowing towards the base The narrowed base on the other hand allows the holding baskets to be more easily stacked, as a very wide top would the stacked holding baskets constantly fall into the nested configuration.

In some embodiments the holding basket further comprises two U-shaped supports each disposed on two opposing side walls extending from the two opposing windows, each U-shaped ending touching one of each opposing windows. Preferably, the two U-shaped supports run parallel to the two rims or the base. The addition of two U-shaped supports further improves the nestibility, by providing an additional support for the bottom of an adjacent holding basket.

In a preferred embodiment the two U-shaped supports of the adjacent holding basket are supported by the two rims of the holding basket. This allows the adjacent holding basket to be at least partially contained within the holding basket while still fully supported by the holding basket in the nestible configuration.

In some embodiments the base and/or the side walls are formed essentially from wire. In some embodiments the basket is formed essentially from wire.

The wire can be metal, preferably a light yet sturdy metal, such as aluminum or steel. Most preferably the metal is further configured to resist processing, e.g. high temperature, pressure and/or humidity. This can be achieved using certain alloys or a coating layer on top of the metal. Additionally or alternatively the wire can be a polymer, preferably a light yet sturdy polymer; more preferably a polymer configured to resist processing.

In some embodiments the metal wire is hollow. Hollow metal wire has the advantage of having low weight. Preferably, the hollow metal wire is made of aluminum or steel. Hollow aluminum or steel wire provides a further weight advantage.

In some embodiments the hollow spaces (apertures) within a horizontal and/or vertical wire may serve as a slot void space for receiving a coupling clip or hook. Thus, in some embodiments the first end and/or the second end of a horizontal and/or vertical metal may be disposed with a slot for receiving the coupling clip or hook. The coupling clip or hook may be used to attach the basket to a second structure, or alternatively, attach baskets placed next to each other.

In some embodiments, the holding basket may be placed onto or inserted into a storage system that is a transport cart or shelve commonly used in the medical industry. In particular the hospital transport or delivery carts may comprise a slidable rack system which can be adjusted to, for instance, the height of the baskets, and wherein a plurality of basket may be slid next to each other.

Since the invention as described herein may be configured to provide an improved safety and security as compared to state of art devices, the invention may thus be transported more safely and securely using various transport devices; provided that said transport devices comprise sufficient and suitable space for storing or sliding said holding basket, and are capable of providing sufficient force for transporting the weight of at least one holding basket; preferably a plurality of holding baskets; more preferably a plurality of holding baskets containing an inner basket and/or medical item; most preferably a plurality of stacked and/or nested holding baskets.

In some embodiments, the holding baskets may be placed into processing systems, designed for cleaning or sterilizing of medical items. An example of a processing system is an autoclave, which is a device that uses steam to sterilize equipment and other objects.

In some preferred embodiment the holding basket is further configured for an autoclave. For example, the wire is configured to allow steam to pass through the holding basket's side walls and/or bottom to reach the contained inner basket and/or medical items.

In some preferred embodiment the inner basket and/or medical items is covered, wrapped or enclosed using a non-woven textile prior to processing. For example, one or more layers of blankets, towels or cloth may be used to partially or completely cover inner basket and/or medical items. Upon entry into an autoclave, the cover will be sterilized together with the holding basket containing the inner basket and/or medical items. After exiting the autoclave, the cover will prevent the inner basket and/or medical items from becoming contaminated or exposed to external factors. This way the holding basket may fulfill the clinical protocols with regards to proper processing of medical items. Additionally or alternatively, the holding basket may also be covered in the same manner.

FIGURES

FIG. 1 is a schematic illustration of a side view of a holding basket (100) as described herein having a top end (102) and a base end (104) comprising a base (110), a first pair of side walls (120, 222) each disposed with a rim (130, 132) at the top end, a second pair of side walls (124) each disposed with a window (140).

Figure 2:
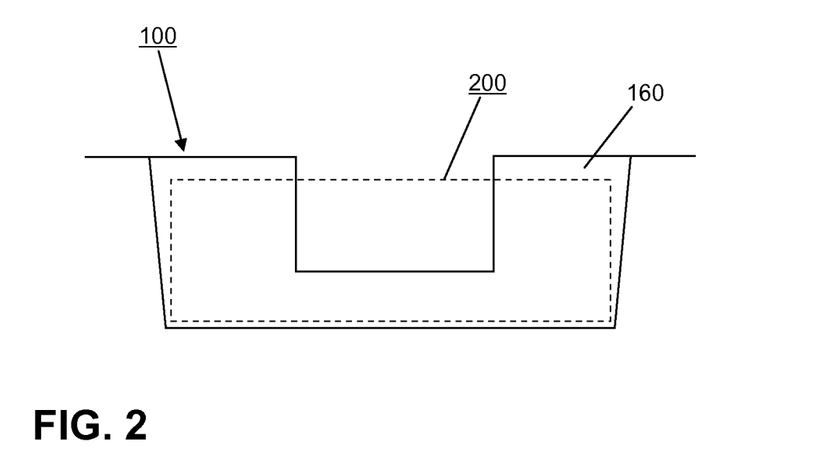
FIG. 2 shows a schematic of a holding basket (100) containing an inner basket (200).

FIG. 2 is a schematic illustration of a side view of a holding basket (100) as described herein wherein a holding space (160) of the a holding basket (100) is occupied with an inner basket (200).

FIG. 3 is a schematic illustration of a side view of a pair of holding baskets, a first holding basket (100) and a second adjacent holding basket (100') in a nested configuration. Imaginary orientation markers (106, 106') are aligned. Each holding basket (100, 100') is provided with a stop member (150, 150') to limit a depth of insertion of the adjacent holding basket (100') into the holding space (160) the first holding basket (100).

FIG. 4 is a schematic illustration of a side view of a pair of holding baskets, a first holding basket (100) and a second adjacent holding basket (100') in a stacking configuration. Imaginary orientation markers (106, 106') are at opposing ends.

Figure 5:
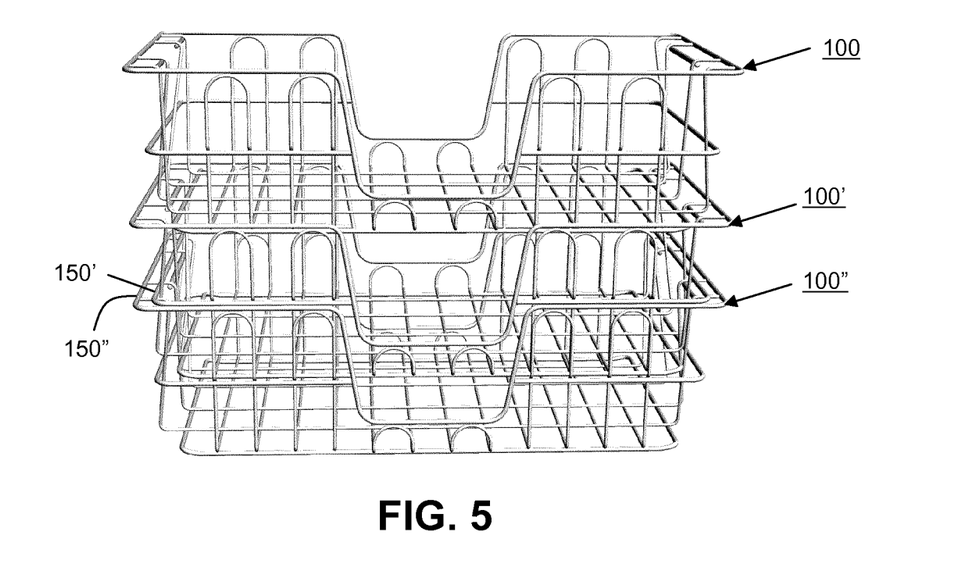
FIG. 5 illustrates how a first holding basket (100) can be stacked on a second holding adjacent basket (100'), while said second adjacent basket (100') is nested in a third holding adjacent basket (100") according to an embodiment of the present invention.

FIG. 5 is a isometric view of three holding baskets (100, 100', 100"), a first (100), second (100') and third (100"), wherein the first (100) and second (100') holding baskets are mutually stacked, and the second (100') and third (100") holding baskets are mutually nested. A stop member (150') on the second (100') holding basket limits the insertion depth of the second holding basket (100') into the holding space of the third holding basket (100").

Figure 6:
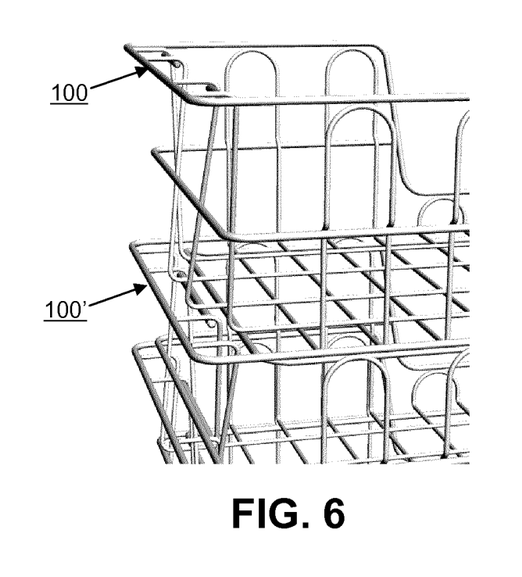
FIG. 6 shows a close-up of FIG. 5, further illustrating the stacking of the first holding basket (100) on the second adjacent holding basket (100')

FIG. 6 is a more detailed isometric view of FIG. 5, showing a part of the base of the first holding basket (100) resting on part of the rim of the second (100') holding basket so as to mutually stack the first (100) and second (100') holding baskets.

Figure 7:
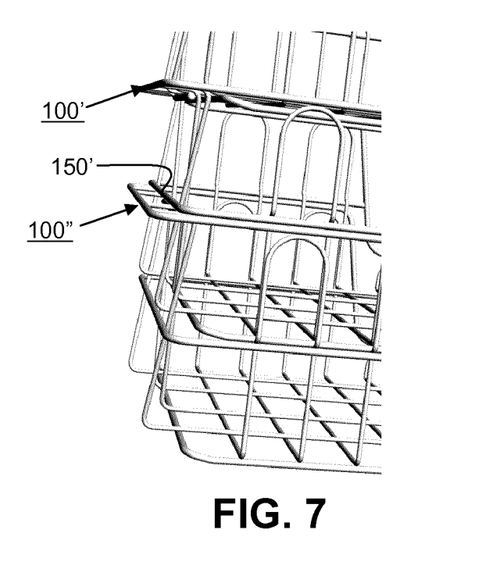
FIG. 7 shows a close-up of FIG. 5, further illustrating the nesting of the second holding basket (100) in the third adjacent holding basket (100').

FIG. 7 is a more detailed isometric view of FIG. 5, showing a part of the stop member (150') of the second holding basket (100') resting on part of the rim of the third holding basket (100") so as limit the depth of nesting insertion into third holding basket (100").

FIG. 8 panel A is a plan view of the top end of a holding basket depicting a pair of opposing rims (130, 132) and an arrangement of tabs (T) and gaps (G). Panel B is a plan view of the base end of a holding basket depicting an inverse arrangement of tabs (T) and gaps (G) compared with the corresponding position on the top edge. In Panel C, a second holding basket (100') is stacked over a first holding basket (100)—the tabs on the base of the second holding basket (100') align and contact the tabs on the top of the first holding basket (100). In Panel D, a second holding basket (100')—rotated 180 deg compared with the second holding basket (100')—is nested inside the first holding basket (100); the tabs of base of the second holding basket (100') slide into the gaps of the first holding basket (100), and the tabs of top of the first holding basket (100) slide into the gaps on the base of the second holding basket (100').

The invention claimed is:

1. A holding basket (100) for containing an inner basket (200) for holding at least one medical item for processing having a top end (102) and a base end (104) comprising:
   an essentially rectangular base (110) and side walls (120, 122, 124) extending from the base (110),
   only two rims (130, 132) configured for sliding into a slide rack each such rim disposed on a first pair (120, 122) of opposing side walls,
   two windows (140) each disposed on a second pair of opposing side walls (124) configured for manual access for slidable removal of the inner basket (200),
   wherein
   the holding basket (100) is configured for both stackability and nestability with an adjacent holding basket (100', 100"), and
   the holding basket has a 180 deg rotational asymmetry about an axis perpendicular to the base (110), such that 180 deg rotation of the holding basket (100) causes:

the rims (130, 132) to appear in the same position before and after the 180 deg rotation, and the holding basket (100) to be stackable or nestable dependent on its 180 deg rotational orientation relative to the adjacent holding basket (100, 100', 100") when the rims (130, 132) of the respective holding baskets (100, 100', 100") are aligned.

2. The holding basket (100) according to claim 1, wherein the base (110) and/or the side walls (120, 122, 124) are formed essentially from wire.

3. The holding basket (100) according to claim 1, wherein each rim (130, 132) is disposed essentially parallel to the base (110).

4. The holding basket (100) according to claim 1, wherein each window (140) has an edge opening at a top end (102).

5. The holding basket (100) according to claim 1, wherein each of the side walls (120, 122, 124) is at least partly tapered, narrowing towards the base end (104).

6. The holding basket (100) according to claim 1 wherein:

each of two opposing edges of the top end (102) of the holding basket (100) is provided with an arrangement of tabs (T) and gaps (G) and the edge at the base end (104) of the holding basket (100) is provided with an inverse arrangement of tabs and gaps compared with the corresponding top edge, an arrangement of tabs and gaps at one of the opposing edges is an inverse of the arrangement of tabs and gaps at other of the opposing edges, said tabs and gaps arranged such that:

the tabs at the base end (104) of an adjacent holding basket (100') align and contact the tabs at the top end of the holding basket (100) such that the adjacent holding basket (100') can stack over the holding basket (100) when the holding basket (100) and the adjacent holding basket (100') adopt a first mutual orientation, and the tabs at the base end (104) of an adjacent holding basket (100') slide into the gaps of the holding basket (100), and the tabs at the top end (102) of the holding basket (100) slide into the gaps at the base end (104) of the adjacent holding basket (100') such that the adjacent holding basket (100') can nest into the holding basket (100) when the adjacent holding basket (100') is rotated 180 deg about an axis perpendicular to the base (110) relative with the holding basket (100) starting from the first mutual orientation.

7. The holding basket (100) according to claim 1, wherein the adjacent basket (100') is a copy of a holding basket (100) of claim 1.

8. A method for sterilising one or more medical equipment items comprising:

placing the one or more medical equipment items into an inner basket (200), placing the inner basket (200) into a holding basket (100) of claim 1, stacking holding basket (100) relative to an adjacent holding basket (100'), sliding the holding basket (100) into a storage system that is a slide rack, placing the storage system into an autoclave and autoclaving, and removing the storage system from the autoclave.

9. Use of the holding basket (100) according to claim 1 for processing medical equipment, wherein the processing includes a step of autoclaving.

\* \* \* \* \*